(12) United States Patent
Mestais et al.

(10) Patent No.: US 6,329,658 B1
(45) Date of Patent: Dec. 11, 2001

(54) DEVICE AND METHOD FOR PROCESSING SIGNALS FROM A RADIATION DETECTOR WITH SEMICONDUCTORS

(75) Inventors: Corinne Mestais, La Terrasse; Alain Chapuis, Martin-le-Vinoux; Olivier Monnet, Tullins; François Lebrun, Champigny S/M, all of (FR)

(73) Assignee: Commissariat A l'Energie Atomique, Paris (FR)

( * ) Notice: Subject to any disclaimer, the term of this patent is extended or adjusted under 35 U.S.C. 154(b) by 0 days.

(21) Appl. No.: 09/355,942
(22) PCT Filed: Feb. 12, 1998
(86) PCT No.: PCT/FR98/00272
  § 371 Date: Sep. 23, 1999
  § 102(e) Date: Sep. 23, 1999
(87) PCT Pub. No.: WO98/36579
  PCT Pub. Date: Aug. 20, 1998

(30) Foreign Application Priority Data

Feb. 14, 1997 (FR) .................................... 97 01745

(51) Int. Cl.$^7$ ........................................ G01J 1/20
(52) U.S. Cl. ................ 250/370.09; 250/370.06; 250/385.1; 257/10; 378/98.2
(58) Field of Search ............. 250/370.09, 385.1, 250/367, 363.2, 370.11, 369, 370.06; 257/10; 378/98.2

(56) References Cited

U.S. PATENT DOCUMENTS 5,440,130 * 8/1995 Cox et al. .................. 250/370.09

FOREIGN PATENT DOCUMENTS

| 0 589 467 | 3/1994 | (EP) . |
| 0 589 467 A2 * | 3/1994 | (EP) . |
| 0 626 590 | 11/1994 | (EP) . |
| 0 637 759 | 2/1995 | (EP) . |

OTHER PUBLICATIONS

L. Verger, et al., The 1996 U.S. Workshop on the Physics and Chemistry of II–VI Materials, 17 pages, "New Developments of CdTe and CdZnTe Detectors For X and γ–Ray Applications," 1996.

J.P Bonnetoy, et al., 9th International Workshop on Room Temperature Semiconductor X and γ Detectors Associated Electronics & Applications, 4 pages, "A Novel ASIC For Readout Electronics In Semiconductor γ–Ray Dectection".

F. Lebrun, et al., Nulcear Instruments and Methods in Physics Research A 000, pps. 1–5, "A CdTe Gamma–Camera For The Space Observatory Integral: Software Charge–Loss Corrections," 1996.

* cited by examiner

Primary Examiner—Robert H. Kim
Assistant Examiner—Pamela R. Hobden
(74) Attorney, Agent, or Firm—Oblon, Spivak, McClelland, Maier & Neustadt, P.C.

(57) ABSTRACT

A system for processing signals from a radiation detector with semiconductors. A plurality of elementary detectors are placed side-by-side along a detection surface or a detection volume in which radiation referred to as incident radiation is capable of giving up its energy in at least one interaction. The device includes the supplying in response to each incident ray, an amount of energy corresponding to the sum of the energies given up during each interaction induced by the incident radiation. This device may be used in medical imaging.

19 Claims, 4 Drawing Sheets

DEVICE AND METHOD FOR PROCESSING SIGNALS FROM A RADIATION DETECTOR WITH SEMICONDUCTORS

BACKGROUND OF THE INVENTION

1. Field of the Invention

This invention relates to a device and method for processing signals from a radiation detector with semiconductors. The invention is applicable more precisely to detectors such as gamma (γ) radiation detectors that comprise a plurality of elementary detectors placed side by side along a surface or a volume of detection.

A device or a method of processing signals conforming to the invention can be used notably in the field of medical imaging for gamma cameras with CdTe or CdZnTe type detectors.

2. Discussion of the Background

FIG. 1 appended shows the principle of operation of an elementary detector with semiconductors of the CdTe type.

The detector in semiconductor 10 is equipped with two electrodes 12, 14 arranged respectively on two opposite faces. The electrodes 12 and 14 act both as polarization electrodes for the detector and as electrodes for reading the detection signals.

To provide the polarization for the detector, the electrodes 12 and 14 are connected respectively to a reference ground potential 16 and to a voltage source 18. The potential difference applied to the opposite faces of the semiconductor allows an electric field to be generated.

Hence, when a ray reaches the semiconductor material and creates an electron-hole pair, these electrical carriers do not recombine but, under the effect of the electric field are driven towards the electrodes 12, 14. An electrical signal is then tapped from these electrodes which is representative of the energy given up by the radiation to the semiconductor.

As FIG. 1 shows, the detection signal taken from electrode 14, is directed to means of processing the signal 24 after having been edited by an amplifier circuit 22.

In the text that follows, any interaction between a ray and the detector, during which the ray gives up to the material all or part of its energy, is referred to as an event.

In a detection head comprising a plurality of elementary detectors placed side by side, the geographic location of events is given by the co-ordinates of the detectors on a detection surface. Hence, an image of the source of radiation, gathered by the detection head can be established by suitable imaging means.

For information on this subject, reference can be made to documents (1), (2) and (3), the references of which are given at the end of this description.

In the case of the detection of gamma (γ) radiation, two types of first order interactions can be distinguished.

In the rest of this text, the first type of interaction during which a gamma ray, called "an incident ray", on reaching the detector, gives up all its energy to the detector material, is referred to as a "photoelectric interaction".

On the other hand, a second type of interaction during which an incident ray only gives up part of its energy, is referred to as a "Compton interaction".

In the text that follows, the radiation coming from an observation target and reaching the detector is referred to as incident radiation. On the other hand, the radiation resulting from a Compton interaction during which the incident radiation only gives up a part of its energy, is referred to as "induced radiation". The induced radiation can also interact with the material and give up its energy to it. In this case, the total energy of the incident radiation is given up in several (generally two) interactions.

When electromagnetic radiation such as a gamma ray reaches a detection head formed by a plurality of elementary detectors placed side by side, three different cases of detection, represented in FIGS. 2A to 2C in very diagrammatic fashion, can be distinguished. For simplification purposes only the elementary detectors are shown in these Figures.

In the first case, illustrated in FIG. 2A, the interaction of a ray 30 with the semiconductor 10 of the detector is an interaction of the photoelectric type as described above. The incident ray 30 gives up all its energy in a single interaction given reference number 31. The detection signal obtained then corresponds to the total energy of the radiation.

In a second case, illustrated in FIG. 2B, the interaction is a Compton interaction. The incident ray 30 gives up a part of its energy during a first interaction labeled with reference number 31 and an induced ray 33 appears. In its turn, the induced ray gives up its energy in a second interaction which, in this example, is of the photo-electric type, labeled with reference number 35. It should be noted that the first and the second interaction both take place in the same elementary detector.

Hence, as these two interactions are quasi-simultaneous, the signal supplied to the detector terminals corresponds finally to the sum of the energies given up during the first and second interactions, that is to say to the energy of the incident radiation 30.

In a third case, illustrated in FIG. 2C, the energy of the incident radiation 30 is also given up during the two interactions 31 and 35. However, in contrast to FIG. 2B, the two interactions 31 and 35 have not taken place in the same detector but in two neighboring detectors 10 and 10a in the detection head.

The signal supplied by the first detector 10 in which the first interaction took place corresponds to the energy given up at the time of the first interaction, that is to say the energy of the incident ray 31 minus the energy of the induced ray. The signal supplied by the second detector 10a only corresponds to the energy of the induced ray, given up to the material during the second interaction. Finally, in this case, neither of the signals from the first or second detectors 10, 10a reflects the energy of the incident ray.

In medical imaging, generally a patient is injected with a radioactive isotope that emits gamma rays with a known and specified energy.

The gamma rays emitted in the patient can also interact with the tissue surrounding the organ of the patient being examined causing Compton type interactions of the type described.

Hence the radiation coming from the patient and reaching the detection head of a gamma ray camera not only includes the radiation from the isotope with known and specific energy but also the induced radiation or "Compton radiation" the energy of which is lower.

In order to prevent the induced or Compton radiation produced in the patient and considered to be parasitic, being taken into account, energy discrimination is carried out at the output from the detectors in such a way that only signals that correspond to the known energy of the radioactive isotope injected into the patient are retained. In other words only the so-called "useful" radiation is retained.

It can therefore be understood that the detection of a ray such as that described in the context of FIG. 2C, is particularly problematical.

In effect, when an incident ray, whose energy is equal to the specified energy that corresponds to the isotope injected into the patient, produces two interactions in two different detectors, the signal received from each detector corresponds to an energy lower than that of the incident radiation as indicated above. These signals are then removed by the energy discrimination operation previously described.

Hence the contribution of a "useful" ray is removed in error since it is taken to be a ray arising from a Compton type interaction within the patient.

Due to the fact that a dose of radioactive product injected into a patient must be relatively limited for health reasons, it may be understood that it is not appropriate to remove too large a number of useful incident rays. In effect as the data acquisition time to form a medical image cannot be too long, particularly for reasons of patient comfort, an over-restricted number of useful rays leads to a deterioration in the quality of the image that is finally obtained.

Therefore this invention proposes to resolve the problem of the loss of information associated with rays which interact in two separate elementary detectors in the detection head.

DESCRIPTION OF THE INVENTION

The subject of this invention is a device for the processing of detection signals from interactions from a radiation detector with semiconductors comprising a plurality of elementary detectors placed side by side along a surface or a volume of detection, at which rays called incident rays, are capable of giving up their energy in at least one interaction, the device comprising means for the management of information in order to deliver, in response to each incident ray, at least one piece of energy data corresponding to the sum of the energies given up at the time of each interaction induced by said ray, incident on a main elementary detector and interaction energies which have substantially one and the same interaction datum and interaction position data that correspond to neighboring elementary detectors.

By detection surface one understands both a flat detection surface and a detection surface which is not flat. In addition, a detection volume is considered which can comprise several detection surfaces which may be overlapped.

An incident ray can interact either with a single elementary detector or with an elementary detector and neighboring elementary detectors.

Thanks to the means referred to as information management means the whole of the incident radiation energy is taken into account, whatever the type of interaction with the detectors.

SUMMARY OF THE INVENTION

Hence, any incident ray having energy that corresponds to the isotope injected into the patient can be taken into account independently of the fact that it may give rise to one or to several interactions.

According to one particular embodiment of the device of the invention, the information management means can comprise;

first means to associate with each interaction detection signal, an elementary detector, interaction position data, interaction energy data and an interaction date datum, selection means to select the interactions that have substantially one and the same interaction date datum and interaction position data that correspond to neighboring elementary detectors in the surface or the volume of detection, and summation means to add the energy data of the selected interactions and to establish a datum called the energy sum datum which corresponds to the sum of the energies given up during each interaction induced by the incident ray.

The position data are determined in relation to the location of the elementary detectors in the surface or the volume of detection. To this end, the first means can comprise at least one circuit capable of supplying position data as a function of the position in the surface or the volume of detection of the elementary detector that has detected said interaction and supplied the signal.

By way of an example, in a detection head of the matrix type, each detector can be labeled by two position co-ordinates. These co-ordinates are then modified as position data at each interaction which has taken place in this detector.

The interaction energy data correspond to the energy given up during each interaction in a given detector. When two interactions arising from one and the same incident ray take place in one and the same elementary detector, the energy datum automatically corresponds to the sum of the energies given up by these two interactions because they are quasi-simultaneous In order to determine the energy data, in particular when the detectors are of the CdTe type, the first means can comprise:

at least one circuit to form the amplitude and the rise time data for the detection signals at least one circuit called a correction circuit to calculate an interaction energy datum as a function of the amplitude and rise time data of the detection signals.

For a more detailed description of the principle of operation of correction circuits, reference may be made to documents (1), (2) and (3) already mentioned.

Finally the interaction date datum allows one to perceive that the interactions are simultaneous. To establish this datum, the first means can comprise at least one counter, controlled by a clock, to supply an interaction date that corresponds to each detection signal.

As previously stated, when an incident ray causes two or more interactions, these interactions are quasi-simultaneous and take place either in one and the same elementary detector, or in nearest neighbor detectors.

Hence, when two interactions take place quasi-simultaneously and in neighboring detectors, it is considered that they arise from one and the same incident ray.

The case in which two interactions due to separate incident rays take place simultaneously in neighboring elementary detectors has a very low probability. This case is not therefore taken into account. Within the energy range considered for use in medical imaging (40–600 keV) and for elementary detectors with a characteristic dimension of the order of a few millimeters, the detectors are considered to be neighboring when they have a common boundary. Hence only "nearest neighbor" detectors are taken into account.

In one particular embodiment of the device of the invention, the selection means can comprise a memory that has a plurality of pages respectively associated with a plurality of successive periods of time or dates, means of writing energy and position data for each interaction respectively on a page whose period of time includes the date of said interaction and means of reading, page by page, the data written into the memory.

By way of example, the period of time associated with each page can correspond to the period of time that separates two successive pulses from a clock, that is to say two successive dates.

In addition, the selection means can comprise position data comparators. These comparators are provided in order to compare the position data written on one and the same page of the memory, that is to say position data that correspond to events having substantially the same date of interaction. Thanks to the comparators it is possible to check if simultaneous interactions come from neighboring elementary detectors or not.

The device of the invention can in addition comprise second means of supplying a datum of a position on the detection surface or detection volume in response to each incident ray.

These second means can be fitted with a calculating device capable of calculating said position datum for the incident ray as a linear combination of the position data of the quasi-simultaneous interactions which have taken place in neighboring elementary detectors. The calculation of the position datum of the incident ray can be weighted as a function of the selected interaction energy data.

In a simplified implementation of the invention, the position datum of the incident ray can be abstracted to one of the positions of one of the interactions, for example, that of the interaction with the greatest energy. The position datum of the incident ray can also be calculated as a barycentric type combination that takes into account all the position data of the interactions induced by this incident ray.

Another subject of this invention is a radiation detector comprising a plurality of elementary detectors placed side by side along the surface or volume of detection and a device for processing detection signals from elementary detectors such as that described above.

According to particular embodiments of the invention, the plurality of detectors can be produced from one or more semiconductor crystals, for example of the CdTe or CdZnTe type.

According to a first possibility, each elementary detector comprises a semi-conductor material and polarization and reading electrodes created on opposite faces of the material.

According to one variant, the detector can also comprise a plurality of electrodes that are separated and placed side by side on at least one face of the material, each electrode forming, with a portion of the material, an elementary detector.

Another subject of the invention is a gamma camera that comprises a radiation detector and a system of forming images such as that described above.

Finally, a subject of the invention is a method of processing interaction detection signals from a radiation detector with semi-conductors comprising a plurality of elementary detectors placed side by side along a surface or a volume of detection, at which the rays, called incident rays, are capable of giving up their energy in one or more interactions, in which, in response to each incident ray, at least one datum is established which is called the energy sum datum and which corresponds to the sum of the energies given up during each interaction induced by said ray.

Other characteristics and advantages of the invention will better emerge from the description that will follow, making reference to the Figures in the appended drawings, which are given purely for illustrative purposes and which are non-limitative.

DETAILED DESCRIPTION OF THE PREFERRED EMBODIMENTS

Figure 3:
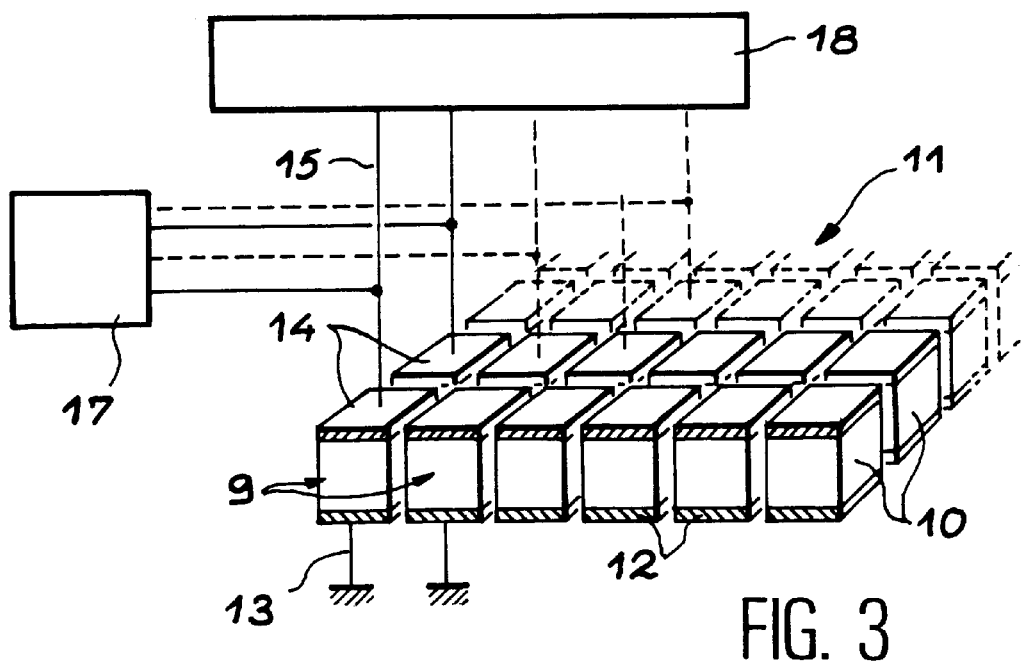
FIG. 3 is a diagrammatic view of a planar detection head that can be used with the device of the invention to form a gamma camera.

FIG. 3 shows an assembly of elementary detectors 9 placed side by side in a detection plane 11 to form a detection head.

Figure 1:
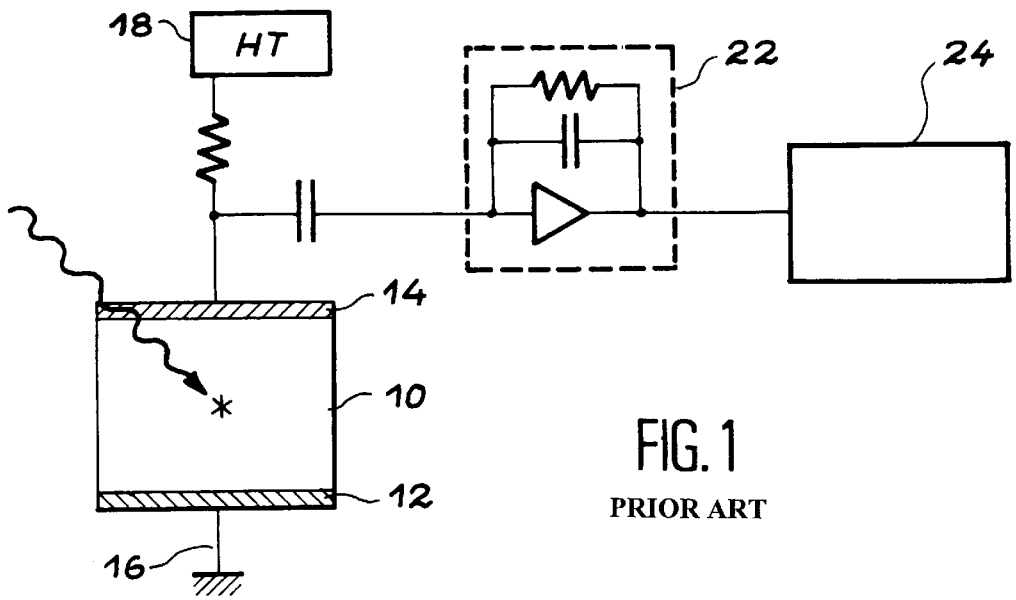
FIG. 1, already described, is a diagram showing the principle of operation of a detector with semiconductors from a detection head.

Each elementary detector is made from an independent block of semiconductor material 10. Reference can be made on this subject to FIG. 1 which has already been described.

Such a head can equip, for example a gamma camera comprising the device of the invention. Each elementary detector comprises a first electrode 12 arranged on one of the faces parallel to the plane of detection. Electrical conductors 13, 15 respectively connect the electrodes of each elementary detector to a device 17 for processing signals conforming to the invention and represented in a non-detailed fashion.

The electrical conductors 13, 15 also connect each elementary detector respectively to ground and to a polarization source 18.

Figure 4:
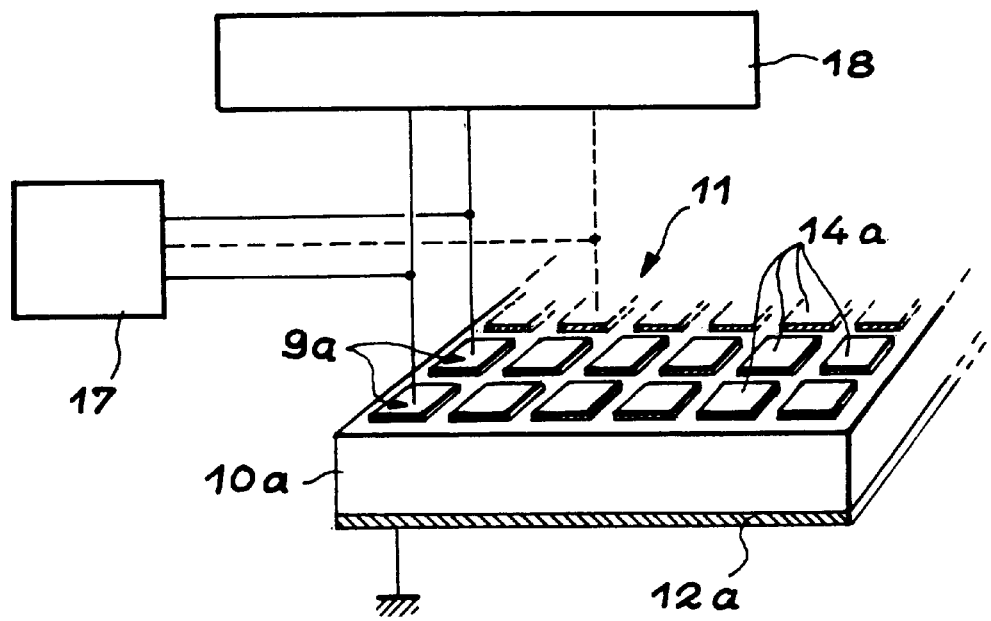
FIG. 4 is a diagrammatic view of another detection head that can also be used with the device of the invention.

According to a variant, illustrated in FIG. 4, a plurality of adjacent detectors 9a are formed in a single block of semiconductor material 10a.

Each detector 9a is defined by an electrode 14a formed on a first face of the crystal. These electrodes 14a are side by side and separated one from the other in such a way that they define a network of elementary detectors 9a.

A counter electrode 12a, common to all the elementary detectors 9a is formed on one opposite face of the crystal 10a.

The electrodes 14a and 12a are provided to polarize the detectors 9a from a polarization source 18 and to collect the detection signals. These signals are directed to a processing unit 17 conforming to the invention.

Figure 5:
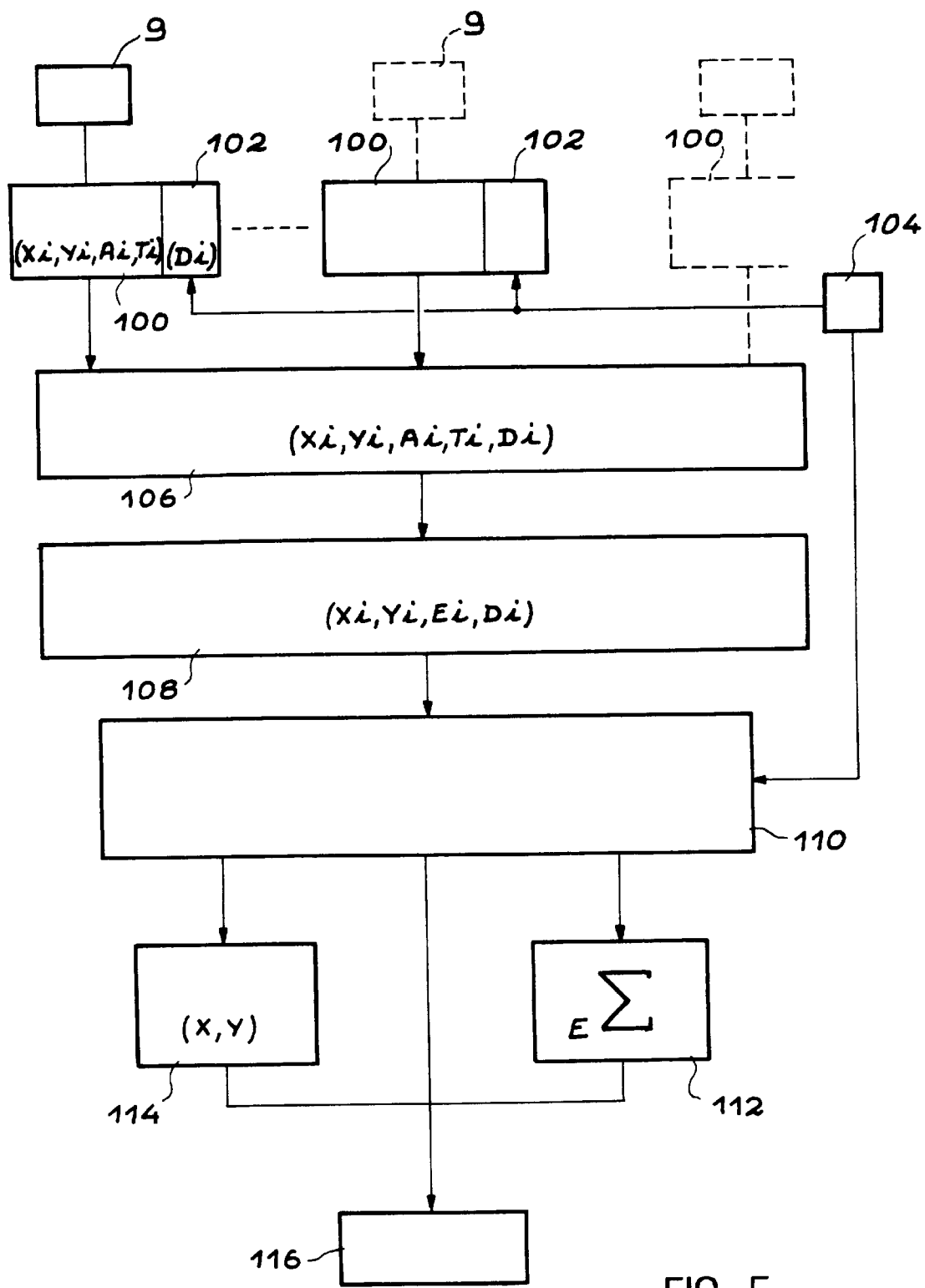
FIG. 5 is a general functional diagram of the device of the invention.

FIG. 5 shows, in more detailed fashion, the main elements of the processing unit 17.

The processing unit comprises a plurality of circuits 100 called interaction data formation circuits, connected respectively to each of the elementary detectors 9 of the detection head.

The data formation circuits have a double function.

A first function is the forming of the detection signals from the elementary detectors. A second function is to associate a data set to each integration signal.

For each signal received, the data formation circuits 100 supply a datum of the position of the interaction in the plane of detection, a datum of the rise time of the signal, a datum of the maximum amplitude of the signal and a date datum.

The position data are simply the co-ordinates $(X_i, Y_i)$ along two directions which correspond to the position on the detection surface of the ($i^{th}$) elementary detector that has supplied the detection signal.

The rise time and maximum amplitude data are directly determined from the detection signal formed.

Finally the date datum is supplied by a dating counter 102 associated with each circuit 100.

The dating counters 102 are connected to a synchronization clock 104.

The dating counters 102, are, for example, 12 bit counters controlled by a clock operating, for example, at a frequency of 10 MHz.

Dating cycles are defined. In the course of such a cycle, the outputs from the dating counters are increased by one unit on each pulse from the clock. At the end of each cycle the counters are reset to zero in order to begin a new dating cycle.

In the given example, with 12 bit counters 102 and a clock 104 operating at 10 MHz, the duration of one dating cycle is of the order of 410 μsec.

The output from each of the interaction data formation circuits 100 is connected to a multiplexer 106 which collects the data corresponding to all the events that take place on the detection head. The data for an event i are noted ($X_i$, $Y_i$, $A_i$, $T_i$, $D_i$) where $X_i$, $Y_i$, $A_i$, $T_i$ and $D_i$ respectively designate the position co-ordinates, the amplitude, the rise time and the date.

The measurement of the energy of the interaction is not supplied directly by the signal from the elementary detectors. Actually, in the semiconductor, the energy deposited by the interaction causes the formation of electron-hole pairs. These charge carriers migrate towards the electrodes of the detector under the effect of an electric field maintained between the electrodes. The mobility of the holes being less than that of the electrons, their contribution to the signal can differ according to the depth of the interaction in the material of the detector. Hence, the signal is not directly usable for the measurement of the energy.

However, thanks to a circuit 108, called the correction circuit, the energy of the interaction is calculated from data $A_i$ of the amplitude of the signal and $T_i$ of the rise time of the signal. The correction circuit 108 is connected to the output from the multiplexer 106.

Hence, the correction circuit establishes for each signal an energy datum designated below by $E_i$ for the interaction i.

At the output from the correction circuit 108, the data $X_i$, $Y_i$, $E_i$ and $D_i$ are directed to selection means 110 the operation of which is explained below making reference to FIG. 6.

The selection means 110 allow one to select the data of interactions that have taken pace approximately at one and the same date and have taken place in neighboring elementary detectors.

In one particular embodiment only the nearest neighbor detectors are considered. This is the case notably when the probability is very low that a second interaction has taken place at a distance greater than the size of one elementary detector from the first interaction induced by the same ray.

The selection of interactions that have taken place in neighboring detectors is carried out by comparator circuits.

By way of example, when one considers two interactions whose position data are ($X_1$, $Y_1$) and ($X_2$, $Y_2$), the following values $\Delta X$ and $\Delta Y$ are defined as:

$\Delta X = |X_1 - X_2|$ $\Delta Y = |Y_1 - Y_2|$ where $|X_1 - X_2|$ and $|Y_1 - Y_2|$ designate the absolute values of the differences.

It is assumed that the interactions have taken place in neighboring detectors if the following equations are verified:

$$\begin{cases} \Delta X = 0 \\ \text{and} \\ \Delta Y = 1 \end{cases} \text{ or } \begin{cases} \Delta X = 1 \\ \text{and} \\ \Delta Y = 0 \end{cases}$$

It is possible for a different definition of neighboring elementary detectors to modify these equations, and to take, for example $\Delta X = \Delta Y = 1$ as an extra criterion for defining neighboring detectors.

Calculation of the values $\Delta X$ and $\Delta Y$ and the verification of the equations defining neighboring elementary detectors can be carried out by a calculating device or by an electronic circuit with comparators specially designed for the task.

The selection means are connected to the summation means 112. These means comprise addition circuits to add the selected interaction energies, that is to say interactions that have taken place quasi-simultaneously in neighboring elementary detectors.

Hence, the energy established for a multiple interaction of the Compton type as described in the introduction part of the text is the sum of the energy given up during two or more successive interactions and is equal to the total energy of the incident ray.

Figure 2A:
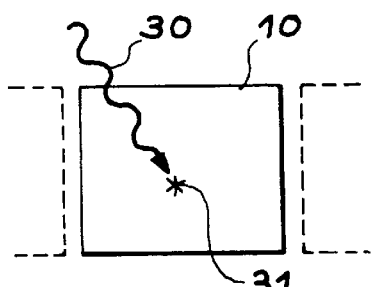
FIGS. 2A, 2B and 2C, already described, are diagrammatic views of detectors with semiconductors and illustrate three types of interactions of an incident ray with the semi-conductor material of the detectors.
Figure 2B:
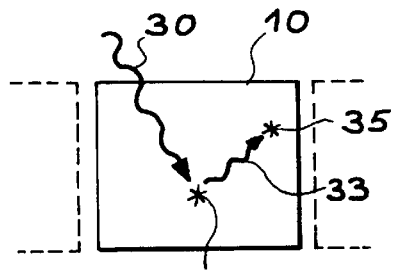
Figure 2C:
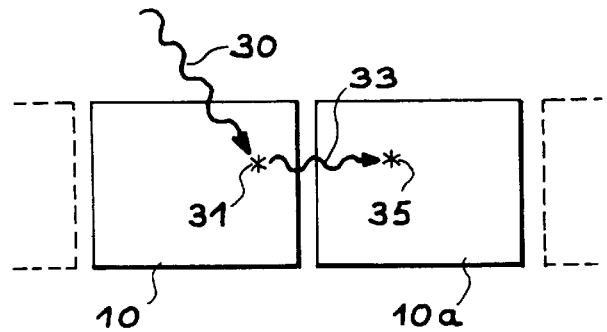

When the position data do not correspond to neighboring detectors, the interactions are interactions of the photoelectric type or Compton only type interactions that have taken place simultaneously in separate detectors. (A "Compton only" interaction has been designated as an interaction like the one shown in FIG. 2C in which the second interaction 35 has not taken place in one of the detectors). These interactions are not selected by the selection means but are processed in the usual way by directing their position and energy data to the imaging means 116 known in itself. In this case, the position and energy data for each interaction are also those of the ray that has caused the interaction.

The selection means 110 are connected to means 114 for calculating a position datum not assigned for the interactions but for the incident ray, the total energy of which is known.

The means 114 for calculating the position datum comprise a calculating device capable of calculating the position datum of the incident ray from the position data of the interactions to which it has given rise.

In a simplified way of working, the position data of the ray can be the co-ordinates of the induced interaction which has the greatest energy.

According to another example, the position data X, Y of the ray can be calculated from the following formulae:

$$X = \frac{X_1 + X_2}{2} \text{ and } Y = \frac{Y_1 + Y_2}{2}.$$

According to a improved way of working, the barycentric calculation can also be weighted as a function of the energy of the interactions. One then has, for example:

$$X = \frac{X_1 \cdot E_1 + X_2 \cdot E_2}{E_1 + E_2} \text{ and } Y = \frac{Y_1 \cdot E_1 + Y_2 \cdot E_2}{E_1 + E_2}$$

In the equations, $X_1$, $Y_1$, $E_1$, $X_2$, $Y_2$, $E_2$ designate the position and energy data respectively from a first and a second interaction caused by an incident ray at one and the same date in neighboring detectors.

The summation means 112 and the means 114 to calculate the position data for the interactions can be connected to an imaging device 116.

The imaging device of a type known of itself allows a gamma image to be formed with the position data and possibly energy data of the incident rays.

Figure 6:
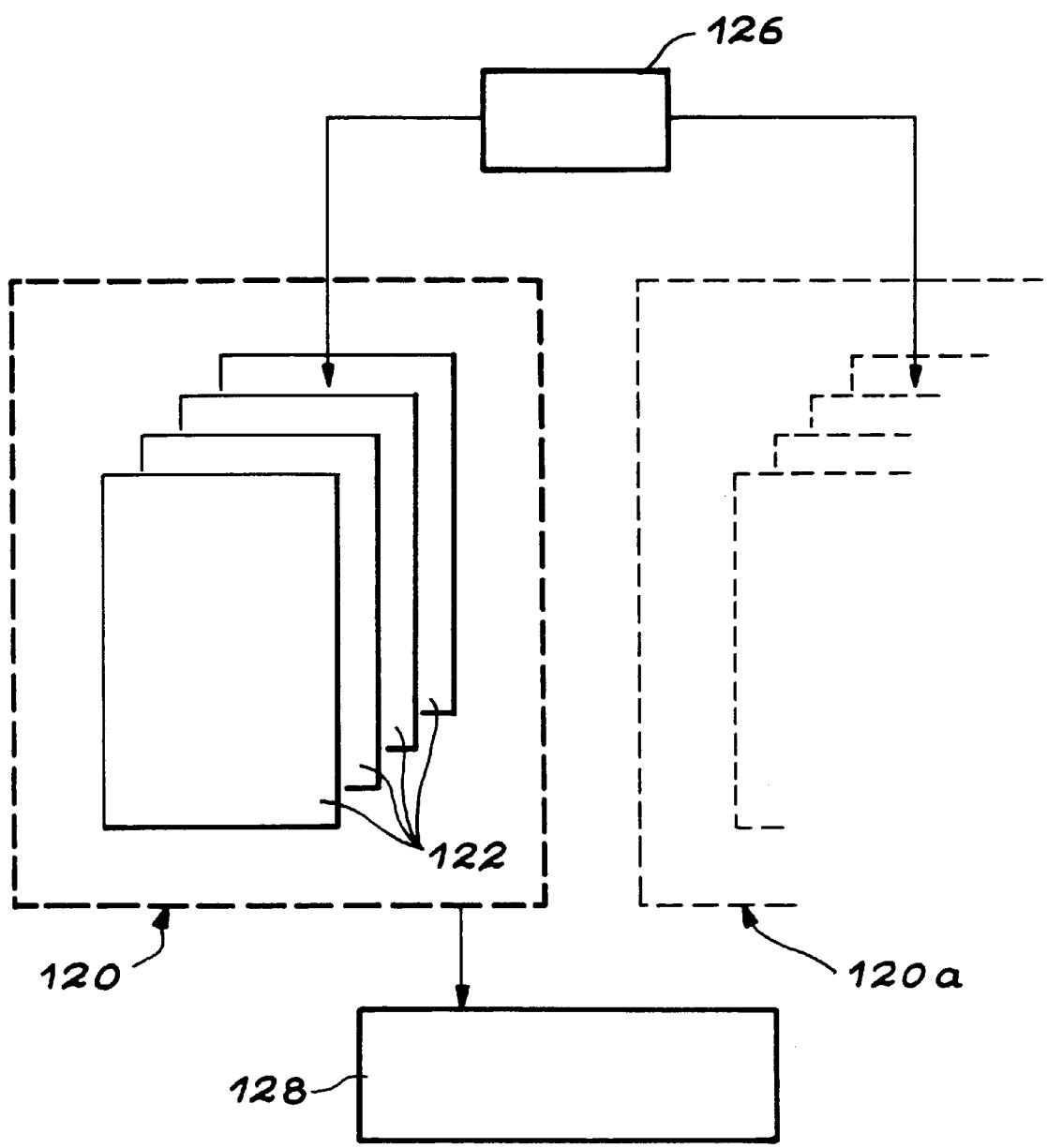
FIG. 6 is a partial detailed diagram of selection means of the device of the invention.

FIG. 6 illustrates diagrammatically the operation of a part of the selection means 110. These means comprise a random access memory (RAM) 120 into which notably position data and energy data of the interactions detected can be written and from which such data can be read.

The memory is subdivided into a plurality of pages 122. More precisely in one particular way of implementing the invention, the number of pages 122 is equal to the number of different possible dates in one dating cycle. By way of example, the memory 120 can comprise 4096 pages and each page corresponds to one date.

When the control clock 104 operates at a frequency of 10 MHz, two successive dates are separated by a time of 100 nsec.

During one dating cycle, the data associated with all the detection signals are written into the memory 120. The address for writing the data is dictated by the date datum $D_i$ associated with each detection signal by a dating counter 102 (see FIG. 5).

Hence, all the data from all the interactions that have taken place on one and the same date $D_i$ are written into the memory on one and the same page that corresponds to that date.

In FIG. 6, reference number 126 indicates a writing register. This register receives the data $(X_i, Y_1, E_i, D_i)$ from the correction means 108 and writes the data $(X_i, Y_i, E_i)$ onto page $D_i$ in the memory.

When the dating cycle is finished, all the dates corresponding to the pages 122 scrolled onto the counters 102 (see FIG. 5). The counters are then reset to zero.

The memory 120 is then read page by page by a reading register that has not been shown. All the data read on one and the same page are considered to correspond to simultaneous events. If the number of events from a page is greater than 1, the data are directed to the comparator circuits 128 of the selection means, to verify whether the data correspond to signals coming from neighboring detectors. When the number of events having data on one and the same page is equal to 1, then there has been just one photoelectric type interaction or a Compton only type interaction. The data are sent directly to the imaging device 116 (see FIG. 5).

Advantageously, the selection means can have several memories available 120, 120a. In this way the memories can operate alternately in such a way that one of the memories can be addressed for the writing of new data while data are being read in the second memory and vice versa.

In a practical embodiment of the processing device of the invention, the group of electronic circuits that provide the functions described above can be produced in the form of an integrated circuit with specific application of the ASIC type.

Documents Quoted (1) The 1996 US Workshop on the Physics and Chemistry of II–VI Materials—Las Vegas 1996 "New Developments of CdTe and CdZnTe detectors for X and γ-ray application" by L. Verger and coll.
(2) 9$^{th}$ International Workshop on Room Temperature Semiconductor X and Detectors, Associated Electronics & Application "A Novel ASIC for Readout Electronics in Semiconductor γ-ray Detection" by J. P. Bonnefoy and coll.
(3) Nuclear Instruments and Methods in Physics Research A 000 (1996) "A CdTe Gamma Camera for the Space Observatory INTEGRAL:Software Charge-loss Corrections" by F. Lebrun and coll.

What is claimed is:

1. A device for processing interaction detection signals for a radiation detector with semiconductors that comprises a plurality of elementary detectors placed side by side along a surface or volume of detection sensitive to the energies given up in one or more interactions by rays called incident rays and which are capable of supplying interaction detection signals characterized in that the device comprises means called processing means to supply, in response to each incident ray detected, at least one energy datum corresponding to the sum of the energies given up during each interaction induced by said incident ray on a main elementary detector and interaction energies having taken place substantially at the same moment on elementary detectors that are neighbors to the main detector.

2. A device according to claim 1, characterized in that the processing means comprise:
   first means to associate with each interaction detection signal, an elementary detector, interaction position data interaction energy data and an interaction date datum,
   selection means to select the interactions that have substantially one and the same interaction date datum and interaction position data that correspond to neighboring elementary detectors in the surface or the volume of detection, and
   summation means to add the energy data of the selected interactions and to establish a datum
   called the energy sum datum which corresponds to the sum of the energies given up during each interaction induced by the incident ray.

3. A device according to claim 2, characterized in that, in addition, it comprises second means to supply, in response to each incident ray, a datum of position on the surface or in the volume of detection.

4. A device according to claim 3, in which, the means of supplying, in response to each incident ray, a position datum, comprise a calculating device capable of calculating said position datum of the incident ray as a linear combination of the interaction position data in relation to the selected interactions energy data.

5. A device according to claim 2, in which, the selection means comprise at least one memory having a plurality of pages respectively associated with a plurality of successive periods of time, means of writing energy and position data for each interaction respectively on a page whose period of time includes the date of said interaction and means of reading, page by page, the data written into the memory.

6. A device according to claim 2, in which, the selection means comprise position data comparators.

7. A device according to claim 2, in which, the first means comprise at least one circuit capable of supplying position data as a function of a location on the surface or the volume of detection of the elementary detector that has detected said interaction.

8. A device according to claim 2, in which, the first means comprise:
   at least one circuit to form the amplitude and the rise time data for the detection signals
   at least one circuit called a correction circuit to calculate an interaction energy datum as a function of the amplitude and rise time data of the detection signals.

9. A device according to claim 2, in which, the first means comprise at least one counter, controlled by a clock to supply an interaction date datum that corresponds to each detection signal.

10. A device according to claim 7 comprising a plurality of circuits to form amplitude and rise time data for the signals, such a circuit being associated with each elementary detector.

11. A device according to claim 8, in which a single common correction circuit is associated with the assembly of elementary detectors and into which a multiplexer is connected between the plurality of circuits for the formation of the amplitude and rise time data for the signals and the correction circuit.

12. A radiation detector comprising a plurality of elementary detectors placed side by side along a surface or a volume of detection and a device for processing detection signals from elementary detectors conforming to claim 1.

13. A radiation detector according to claim 12, in which each elementary detector includes a semiconductor detection material and polarization and reading electrodes created on opposite faces of the detector.

14. A radiation detector according to claim 12 comprising at least one semiconductor detection material and a plurality of electrodes separated and placed side by side on at least one face of the semiconductor material, each electrode forming with a portion of the semiconductor material, an elementary detector.

15. A detector according to one of claim 13, in which the semiconductor material is a crystal of CdTe or CdZnTe.

16. A gamma camera comprising a radiation detector and a system for forming images characterized in that the radiation detector conforms to claim 12.

17. A method of processing interaction detection signals from a radiation detector with semiconductors comprising a plurality of elementary detectors placed side by side along a surface or a volume of detection, sensitive to the energies given up in one or more interactions by the rays, called incident rays, and capable of supplying interaction detection signals, characterized in that:

one associates with each interaction detection signal from an elementary detector, position data for the interaction and a date datum for the interaction one selects interactions having one and the same interaction date datum and interaction position data that correspond to elementary detectors that are neighbors on the surface or volume of detection, and one adds the energy data of the selected interactions and one establishes a datum called an energy sum datum that corresponds to the sum of the energies given up during each interaction induced by the incident ray.

18. A method according to claim 17, in the case of a detection surface, in which, in addition to a position datum in response to each incident ray, one establishes the position datum that corresponds to a linear combination of position data for the interactions on the detection surface as a function of energies of the interactions induced by the ray.

19. A detector according to claim 14, in which the semiconductor material is a crystal of CdTe or CdZnTe.

* * * * *